(12) United States Patent
Salehi

(10) Patent No.: US 10,076,341 B2
(45) Date of Patent: Sep. 18, 2018

(54) VARIABLE ANGLE SURGICAL INSTRUMENT AND METHOD OF USE

(71) Applicant: NEUROENTERPRISES, LLC, Chicago, IL (US)

(72) Inventor: Sean A. Salehi, Chicago, IL (US)

(*) Notice: Subject to any disclaimer, the term of this patent is extended or adjusted under 35 U.S.C. 154(b) by 602 days.

(21) Appl. No.: 14/640,948

(22) Filed: Mar. 6, 2015

(65) Prior Publication Data

US 2015/0250484 A1    Sep. 10, 2015

Related U.S. Application Data

(60) Provisional application No. 61/967,079, filed on Mar. 10, 2014.

(51) Int. Cl.
*A61B 17/122* (2006.01)
*A61B 17/16* (2006.01)

(52) U.S. Cl.
CPC ...... *A61B 17/1608* (2013.01); *A61B 17/1671* (2013.01)

(58) Field of Classification Search
CPC .. A61F 6/204; A61F 6/206; A61F 2002/4622; A61F 2002/4628; A61B 5/6838; A61B 17/122; A61B 17/1606; A61B 17/1608; A61B 2017/2908
See application file for complete search history.

(56) References Cited

U.S. PATENT DOCUMENTS

2003/0158576 A1* 8/2003 Nagase ................ A61B 17/29
606/205
2003/0212435 A1* 11/2003 Gold .................... A61B 17/122
606/206

* cited by examiner

*Primary Examiner* — Christopher D Prone
(74) *Attorney, Agent, or Firm* — J. Peter Paredes; David G. Rosenbaum; Rosenbaum IP, P.C.

(57) ABSTRACT

A Variable Angle Surgical Instrument is disclosed and generally comprises: a rail portion including a proximal end, a distal end, and a longitudinal axis extending therebetween; a jaw portion operably coupled to the distal end of the rail portion; wherein the jaw portion rotates to variable angles relative to the longitudinal axis, and the jaw portion operates between a closed position and an open position to clamp down and remove tissue; a locking mechanism operably coupled to the rail portion to lock the jaw portion to an angled position.

12 Claims, 10 Drawing Sheets

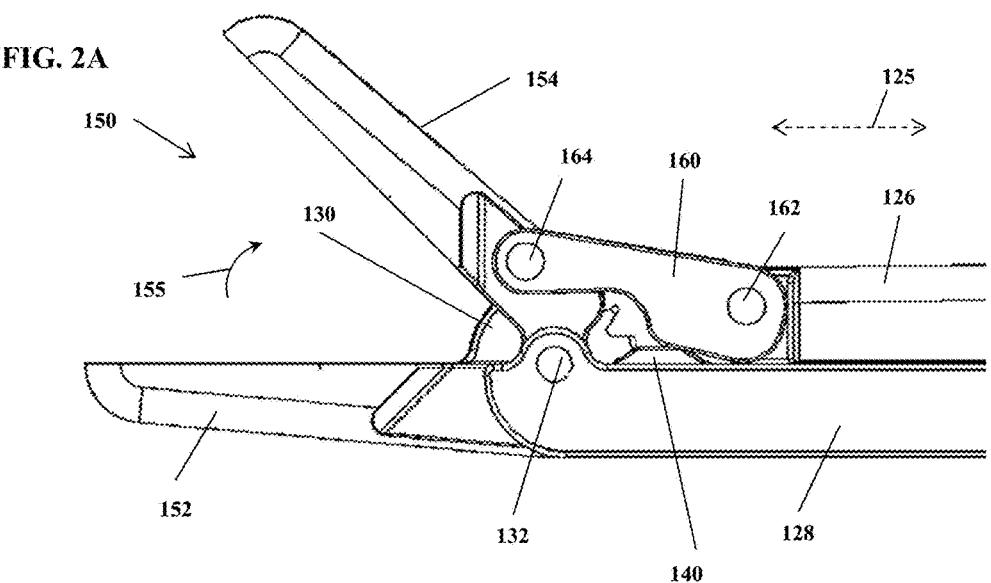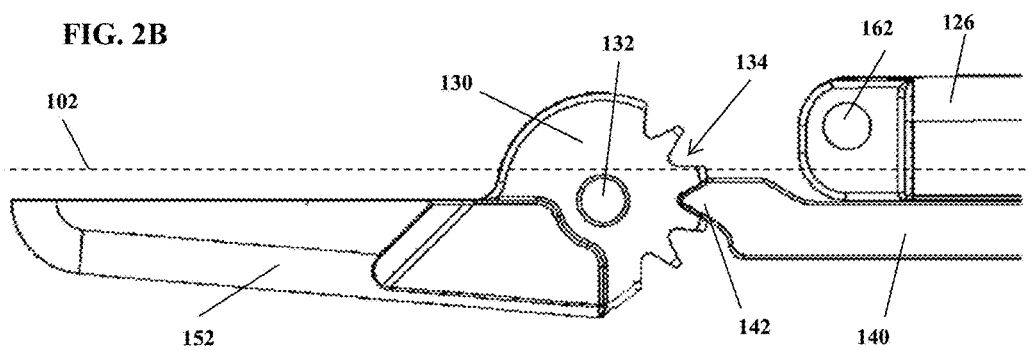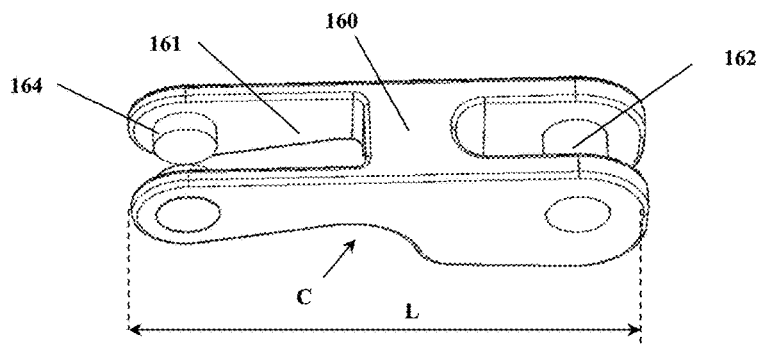

US 10,076,341 B2

VARIABLE ANGLE SURGICAL INSTRUMENT AND METHOD OF USE

CROSS-REFERENCE TO RELATED APPLICATIONS

The present application claims priority from U.S. Provisional Application Ser. No. 61/967,079, filed Mar. 10, 2014, herein incorporated by reference in its entirety.

BACKGROUND

The present invention relates generally to rongeurs and, more particularly, to rongeurs and methods for removing tissue from a region of the spine of a patient.

It is well known to use rongeurs to remove tissue, e.g., nucleus pulposus, from a region of the spine. Rongeurs are surgical instruments for the cutting away of human tissue, and most commonly, cartilage and/or bone. Rongeurs are known to be used in the spinal canal and about delicate neural structures.

A rongeur with an elongated shaft may be inserted into the intervertebral space of a patient. Jaws on the end of the rongeur may be closed around a portion of the tissue to be removed, a portion of the material may be bitten off by the jaws of the rongeur and the rongeur may be removed from the intervertebral space removing the portion of the material held between the jaws of the rongeur.

Current rongeurs come in fixed angles such as straight 30-45 degrees up or 30-45 degrees down. The present invention attempts to solve this problem, as well as others.

SUMMARY OF THE INVENTION

Provided herein are systems, methods and apparatuses for a variable angle surgical instrument comprising: a rail portion including a proximal end, a distal end, and a longitudinal axis extending therebetween; a jaw portion operably coupled to the distal end of the rail portion; wherein the jaw portion rotates to variable angles relative to the longitudinal axis, and the jaw portion operates between a closed position and an open position to clamp down and remove tissue; a locking mechanism operably coupled to the rail portion to lock the jaw portion to an angled position.

A method of using a Variable Angle Surgical Instrument, comprising: disengaging an adjustment rod operably coupled with a ratchet and a jaw portion and rotating the jaw portion of the Variable Angle Surgical Instrument to a proper angle relative to the longitudinal axis of the Variable Angle Surgical Instrument; opening the jaw portion by longitudinally translating a top rail portion towards the proximal end of the Variable Angle Surgical Instrument by rotation of a handle; placing the opened jaw portion around a portion of the tissue to be removed; moving the jaw portion to a closed position to at least partially close around tissue and secure tissue within a grooved portion of the jaw portion.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 2A is a side view of the jaw portion in the open position.

FIG. 2B is a side view of the first jaw operably coupled with the adjustment rod with the second jaw, bottom rail portion, and the link arm removed.

FIG. 2C is a top perspective view of the link arm.

DETAILED DESCRIPTION OF THE INVENTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient.

The Variable Angle Surgical Instrument may be used in arthroscopic, orthopedic, or endoscopic surgery to remove or treat human tissue. In one embodiment, the Variable Angle Surgical Instrument operates as a Pituitary Rongeur to decompress disc space of centrally herniated discs.

Figure 1A:
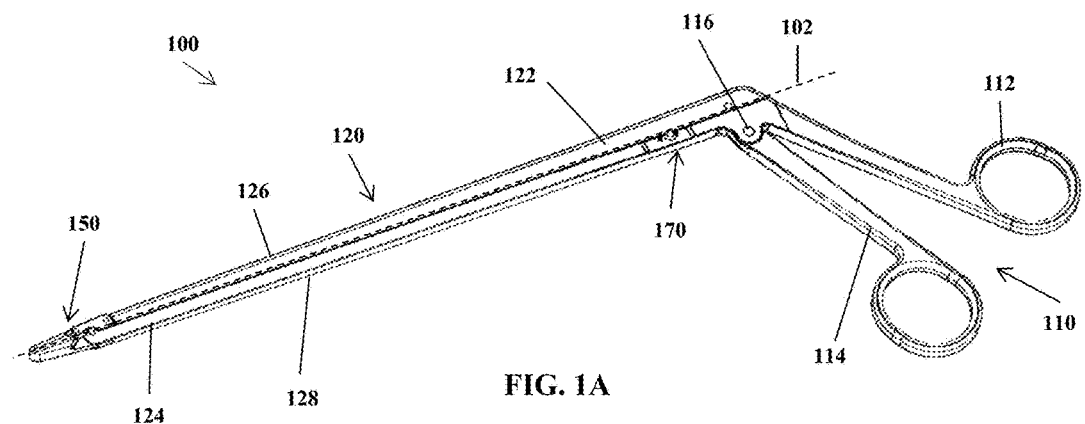
FIG. 1A is a perspective view of the Variable Angle Surgical Instrument in the closed position and 0 degree position for the jaw portion.
Figure 1B:
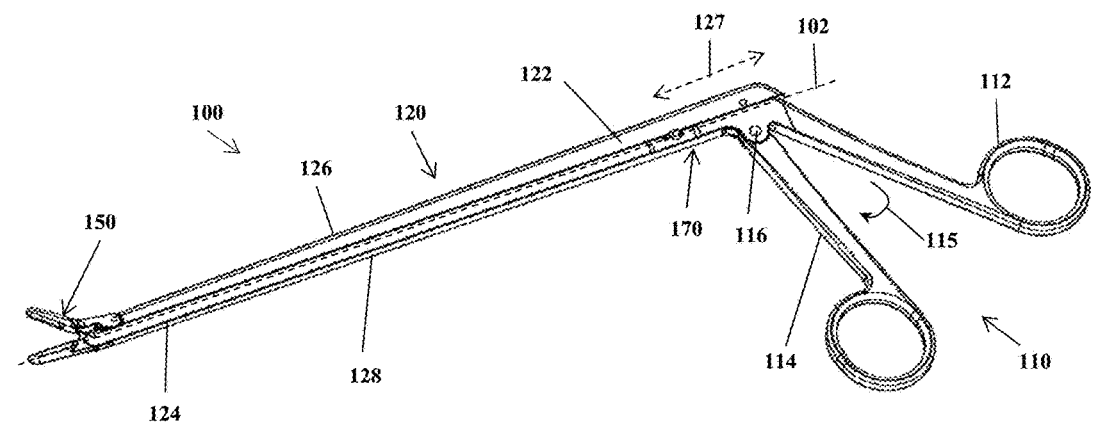
FIG. 1B is a perspective view of the Variable Angle Surgical Instrument in the open position and 0 degree position for the jaw portion.

Generally speaking, the Variable Angle Surgical Instrument 100 generally comprises a handle 110 operably coupled with a proximal end 122 of a rail portion 120 and a jaw portion 150 operably coupled to a distal end of 124 the rail portion 120, as shown in FIG. 1A. The Variable Angle Surgical Instrument 100 generally includes a longitudinal axis 102 running along the proximal portion to the distal portion of the Variable Angle Surgical Instrument 100. The jaw portion 150 is rotatable and rotates to variable angles along the longitudinal axis of the Variable Angle Surgical Instrument 100. Variable Angle Surgical Instrument 100 includes a locking mechanism 170 generally coupled between the rail portion 120 and the handle 110 that adjusts the jaw portion 150 rotational position along the longitudinal axis and locks the jaw portion 150 once rotated to proper position. The jaw portion 150 is at the 0 degree position is shown in FIG. 1A, whereby the jaw portion 150 is substantially parallel with the longitudinal axis 102 of the Variable Angle Surgical Instrument 100. The jaw portion 150 also operates between an open and closed position to clamp down and remove tissue as needed by an operator. The handle 110 operates to open the jaw portion 150. The open position of the jaw section is shown in FIG. 1B. In one embodiment, the jaw portion 150 may decompress disc space between invertebrate, as described below. The rail portion 120 includes top rail portion 126 operably coupled with a bottom rail portion 128. The handle 110 includes a first handle 112 rotatably coupled with a second handle 114 by way of a pin 116. The first handle 112 is operably coupled with the bottom rail portion 128 and the second handle 114 is operably coupled with the top rail portion 126. The second handle 114 rotates about the first handle 112 in the direction of arrow 115 as to longitudinally translate the top rail 126 in the direction of arrow 127, which then opens the jaw portion 150, as further described below.

As shown in FIG. 2A, the jaw portion 150 generally comprises a first jaw 152 rotatably coupled with a second jaw 154, and the first jaw is rotatably coupled with the bottom rail portion 128. The first jaw 152 and the second jaw 154 rotate together by way of a ratchet 130 fixedly coupled to the first jaw 152 and an adjustment rod 140 longitudinally disposed within the bottom rail portion 128, as shown in FIG. 2B. The adjustment rod 140 is longitudinally coupled within the bottom rail portion 128 and translates longitudinally or along the longitudinal axis. In one embodiment, the ratchet 130 is fixedly attached to the first jaw 152, and alternatively, the ratchet 130 may be integrally formed with the first jaw 152. The ratchet 130 is rotatable about pin 132 connected to the bottom rail portion 128, such that the ratchet 130 rotates the first and second jaw 152, 154 along the longitudinal axis. The second jaw 154 is rotatably coupled with a link arm 160 as to open and rotate the second jaw 154 with respect to the first jaw 152, as generally shown by arrow 155 in FIG. 2A. The link arm 160 is operably coupled with the distal end of the top rail portion 126 by way of a pin 162, which allows the proximal end of the link arm 160 to rotate about pin 162. The link arm 160 is operably coupled with the proximal end of the second jaw 154 by way of a pin 164, which allows the distal end of the second jaw 154 to rotate relative to the first jaw 152 and the longitudinal axis of the Variable Angle Surgical Instrument 100. The top rail portion 126 translates longitudinally or along the longitudinal axis as shown by arrow 125 by rotation of the second handle 114, as further described below. In one embodiment, the link arm 160 includes a length L and a curvature C along the distal portion of the link arm 160, as shown in FIG. 2C. The length L of the link arm may be selected as to allow the jaw portion 150 to rotate to +100 degrees to −100 degrees. The curvature C of the link arm 160 may be selected to allow for the negative degree rotation of the jaw portion 150 as to not interfere with distal end of the bottom rail portion 128. The link arm 160 may include a slotted region 161 along the distal portion, whereby the proximal end of the second jaw 154 sits within the slotted region 161 and is able to rotate within the slotted region 161. In one embodiment, the slotted region 161 approximates the width of the second jaw 154.

As shown in FIG. 2B, the adjustment rod 140 includes a distal end that includes a lip portion 142 that substantially engages the ratchet 130. The ratchet 130 includes a plurality of detents 134 along the circumference of the ratchet 130, whereby the lip portion 142 substantially engages a single detent 134 to lock the first jaw 152 along the longitudinal axis of the Variable Angle Surgical Instrument 100. The plurality of detents 134 are located around the circumference of the ratchet 130 as to allow the first jaw 152 and the jaw portion 150 to rotate above and below the longitudinal axis 102 from about +100 degrees to −100 degrees. The detents 134 may be selected as to rotate the jaw portion to a specific degree along the longitudinal axis, as will be further described below. The lip portion 142 substantially mates with the detent 134 and approximates it's generally size and configuration. In one embodiment, the detent 134 assumes a general curved teeth configuration; alternative configurations for the detent may be a square or rectangular configuration depending on the locking mechanism desired.

Figure 3A:
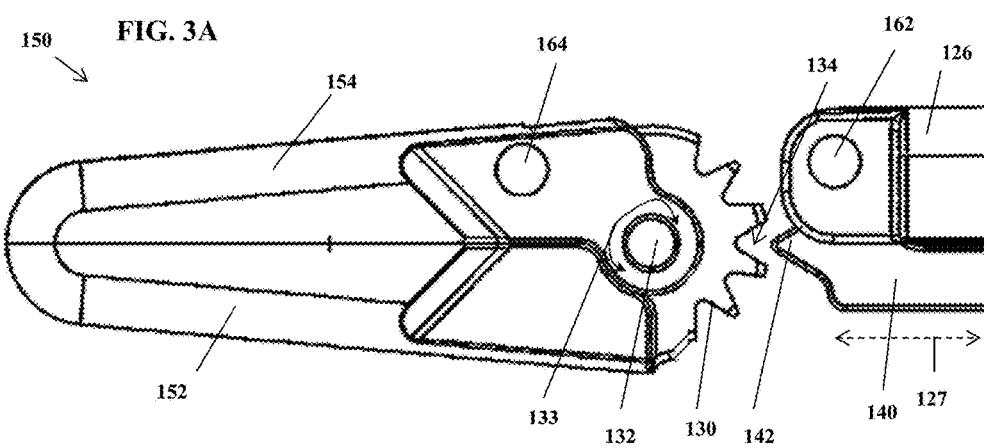
FIG. 3A is side view of the jaw portion in the closed position with the adjustment rod disengaged from the ratchet and the link arm and bottom rail portion removed.
Figure 3B:
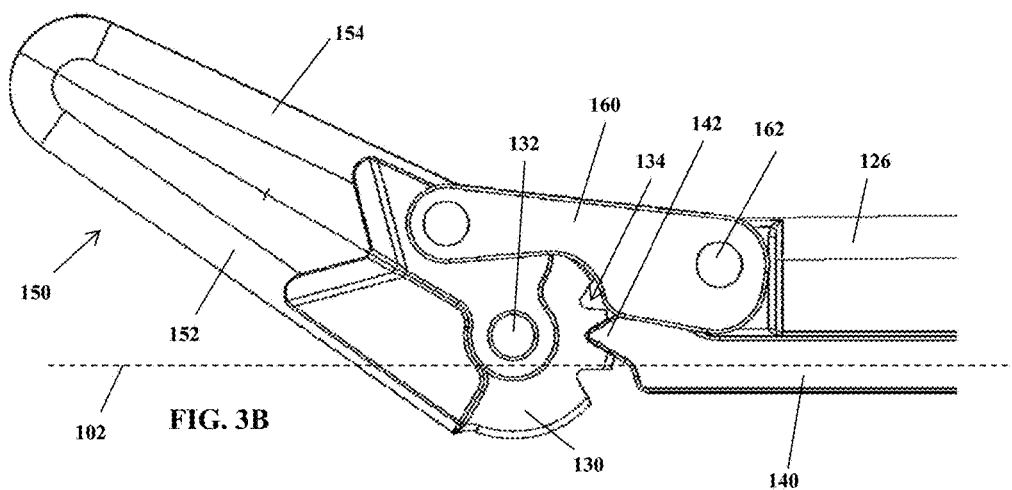
FIG. 3B is side view of the jaw portion in the closed position with the adjustment rod engaged with the ratchet, while the bottom rail portion is removed.

As shown in FIG. 3A, when the adjustment rod 140 is translated proximally towards the handle in the direction of the arrow 127 by operation of the first handle 114, the lip portion 142 of the adjustment rod 140 disengages from the detent 134 as to allow the ratchet 130 and the jaw portion 150 to rotate clockwise or counterclockwise about pin 132 in the direction of arrow 133. Each detent 134 allows a specific degree of rotation for the jaw portion 150 to rotate and be locked by the adjustment rod 140. Once the jaw portion 150 is rotated to a specific angle, the adjustment rod 140 is translated distally towards the ratchet 130 and the lip portion 142 engages a specific detent 134 as to lock the jaw portion 150 into a specific angle, as shown in FIG. 3B. The angle of rotation of the jaw portion 150 as shown in FIG. 3B is about 30 degrees from the longitudinal axis 102 of the Variable Angle Surgical Instrument 100.

Figure 3C:
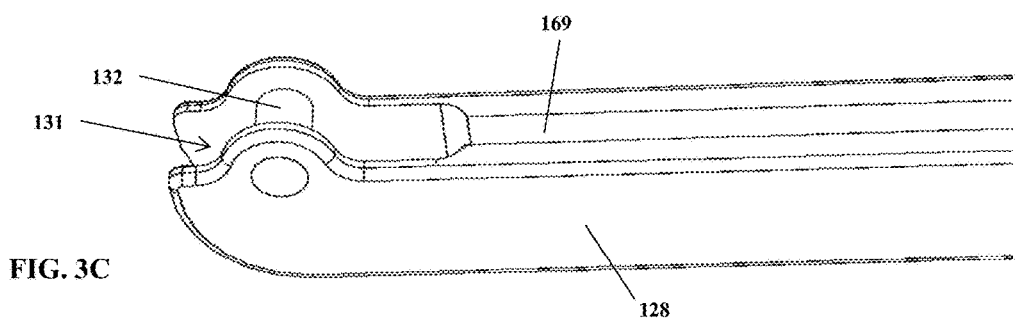
FIG. 3C is a top perspective view of the bottom rail portion.

As shown in FIG. 3C, the bottom rail portion 128 includes a longitudinal cavity 169 extending from the proximal end to the distal end of the bottom rail portion 128, in which the adjustment rod 140 is operably disposed within longitudinal cavity 169 and able to longitudinally translate towards the proximal end and distal end of the bottom rail portion 128. The distal end of the bottom rail portion 128 includes a slotted region 131 that allows the ratchet 130 to rotate about pin 132 on the distal end of the bottom rail portion 128.

Figure 4A:
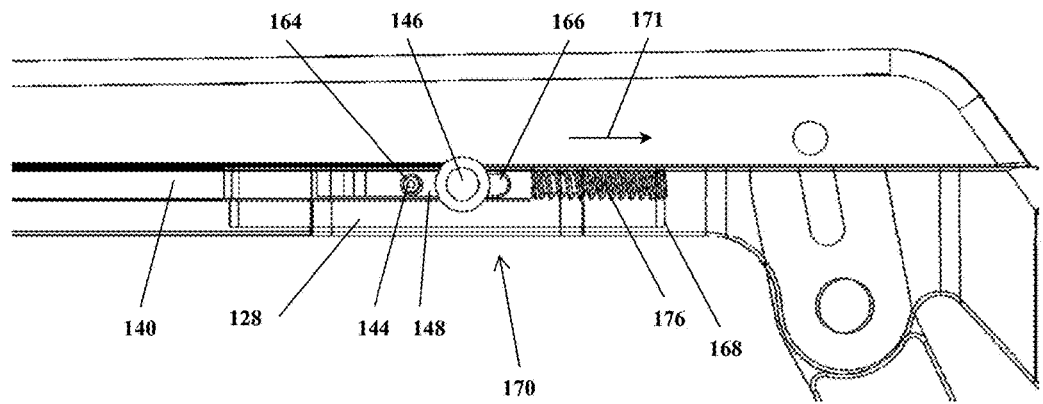
FIG. 4A is a side view of the locking mechanism showing the adjustment rod coupled with the bottom rail portion in the locked position.
Figure 4B:
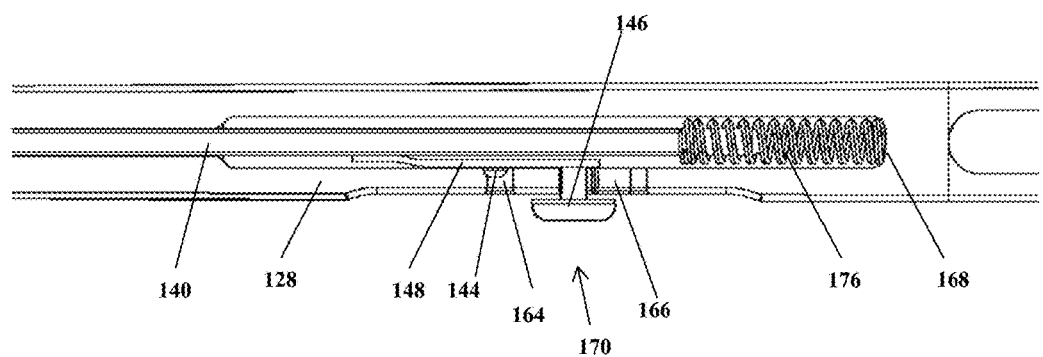
FIG. 4B is a top view of locking mechanism showing the adjustment rod coupled with the bottom rail portion.
Figure 4C:
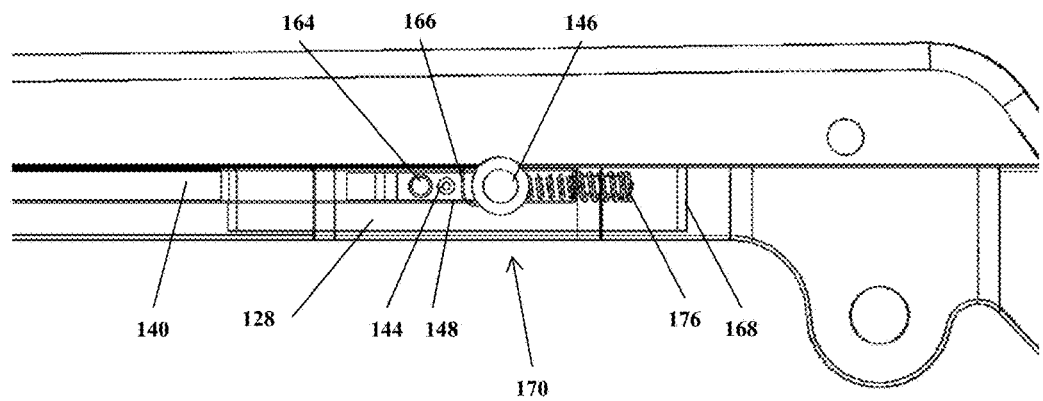
FIG. 4C is a side view of the locking mechanism showing the adjustment rod coupled with the bottom rail portion in the unlocked position.
Figure 5A:
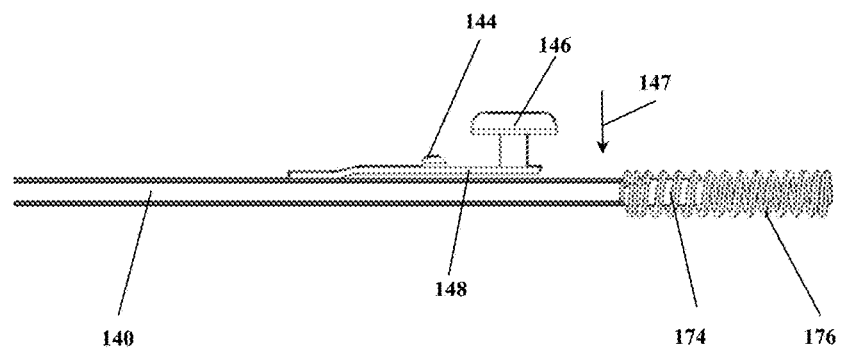
FIG. 5A is a top view of the proximal end of the adjustment rod showing the button and detent coupled with the spring tab for the locking mechanism.
Figure 5B:
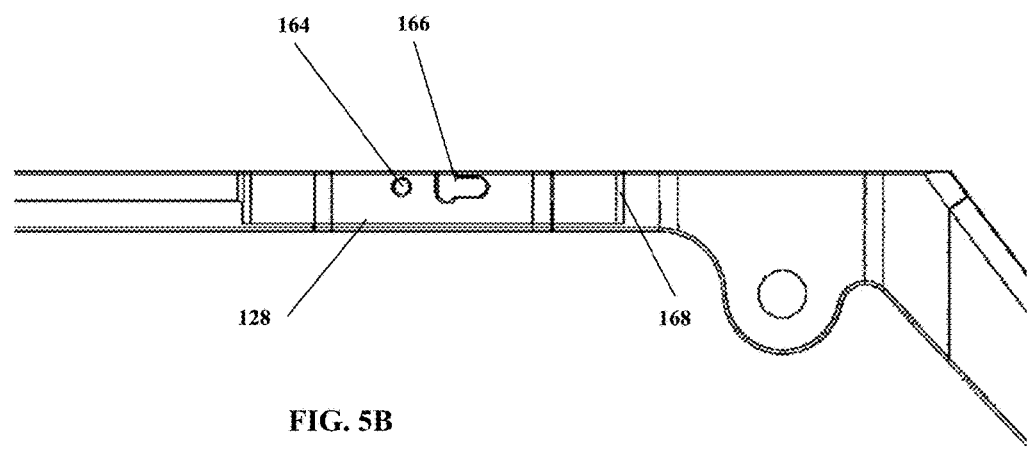
FIG. 5B is side view of the bottom rail portion showing the opening and grooved portion of the locking mechanism
Figure 5C:
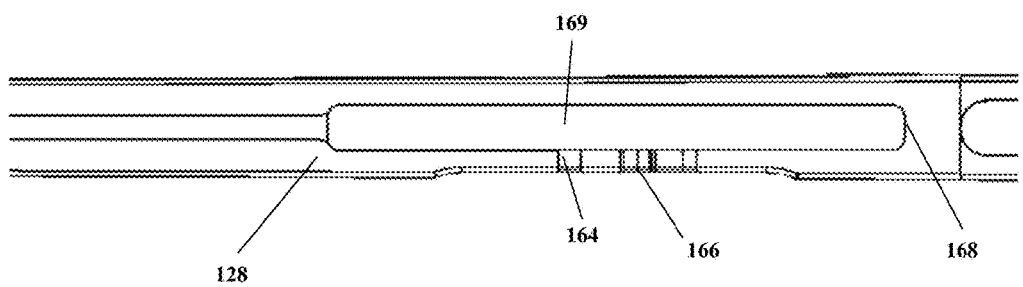
FIG. 5C is a top view of the bottom rail portion showing the open cavity where the adjustment rod is disposed.

As shown in FIGS. 4A-4B, the adjustment rod 140 includes a proximal portion operably coupled with the locking mechanism 170 and the bottom rail portion 128. The proximal portion of the adjustment rod 140 includes a detent 144 and a button 146 protruding from the bottom rail portion 128. The button 146 protrudes from a grooved region 166 disposed through the surface of the bottom rail portion 126, as shown in FIG. 5B, such that the button 146 is able to longitudinally slide towards proximal end 168 of the bottom rail portion 128. The detent 144 locks into a hole 164 disposed on the inner surface of the bottom rail portion 128, as shown in FIG. 5B. The detent 144 and hole 164 serve to lock the adjustment rod 140 from longitudinally moving. The detent 144 and button 146 are both disposed on top of a spring tab 148, as shown in FIG. 5A, which serves to bias the detent 144 towards the hole 164 and the button 146 towards the exterior surface of the bottom rail portion 128. A spring 176 operably coupled with the proximal end of the adjustment rod 140 and the proximal end of the bottom rail portion 128, and the spring 176 serves to bias the adjustment rod 140 towards the distal end of the Variable Angle Surgical Instrument 100. In one embodiment, the proximal end of the adjustment rod 140 includes a spring coupled section 174, such that the spring 176 is fixedly engaged with the proximal end 168 of the adjustment rod 140, as shown in FIG. 5A. A user or operator pushes the button 146 towards the interior in the direction of arrow 147, as to displace the detent 144 from the hole 164 and translate the adjustment rod 140 towards the proximal end of the Variable Angle Surgical Instrument 100 generally shown in the direction of arrow 171, as shown in FIG. 4C. By longitudinally translating the adjustment rod 140 and button 146 towards the proximal end of the Variable Angle Surgical Instrument 100, the jaw portion 150 may be free to rotate to its desired angle. The user or operator then releases the button 146 such that the spring 176 biases the adjustment rod 140 and the lip portion 142 into the detent 134 of the ratchet 130 and lock the jaw portion 150 into an angled position. The detent 144 is then able to lock with the hole 164 of the bottom rail portion 128 and prevent any further longitudinal movement until the button 146 is pushed by a user or operator. The adjustment rod 140 is disposed within a longitudinal cavity 169 located within the bottom rail portion 128, as shown in FIG. 5C. The proximal end of the longitudinal cavity 169 includes a greater width than the middle portion of the longitudinal cavity 169, such that the proximal end adjustment rod 140 and spring tab 148 is disposed within the proximal end of the longitudinal cavity 169.

Figure 6A:
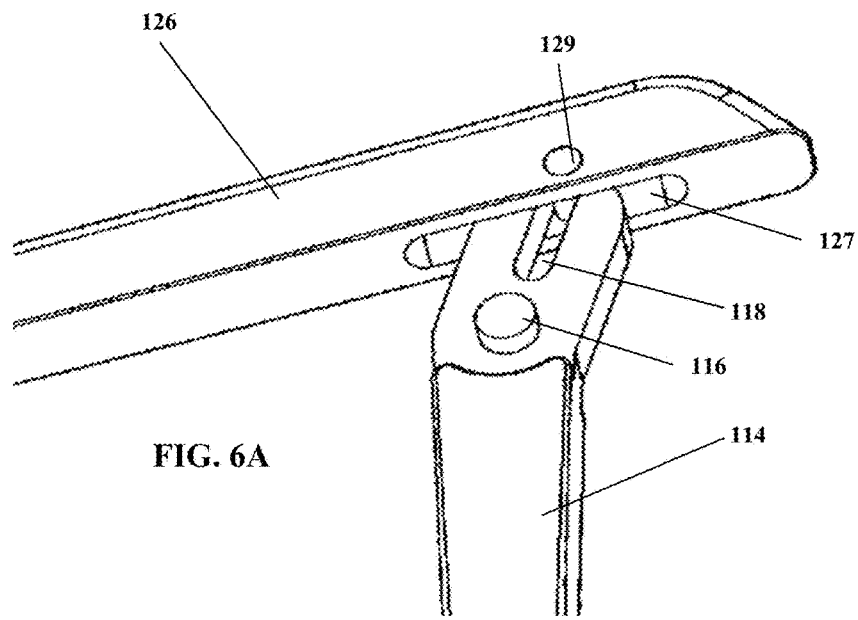
FIG. 6A is perspective bottom view of the top rail portion coupled with the second handle, whereby the bottom rail portion is removed.

As shown in FIG. 6A, the second handle 114 include a top slotted portion 118 operably coupled with the proximal end of the top rail portion 126. The proximal end of the top rail portion 126 includes a slotted portion 127 and a pinned portion 129, by which the second handle 114 longitudinally translates the top rail portion by rotation of the second handle 114 about pin 116. The distal end of the second handle 114 pushes or translates pin 129 as to translate the top rail portion 126 and the top slotted portion 118 allows the pinned portion 129 to longitudinally move or translate. The slotted region 127 includes a width as to receive and couple the distal end of the second handle 114.

Figure 6B:
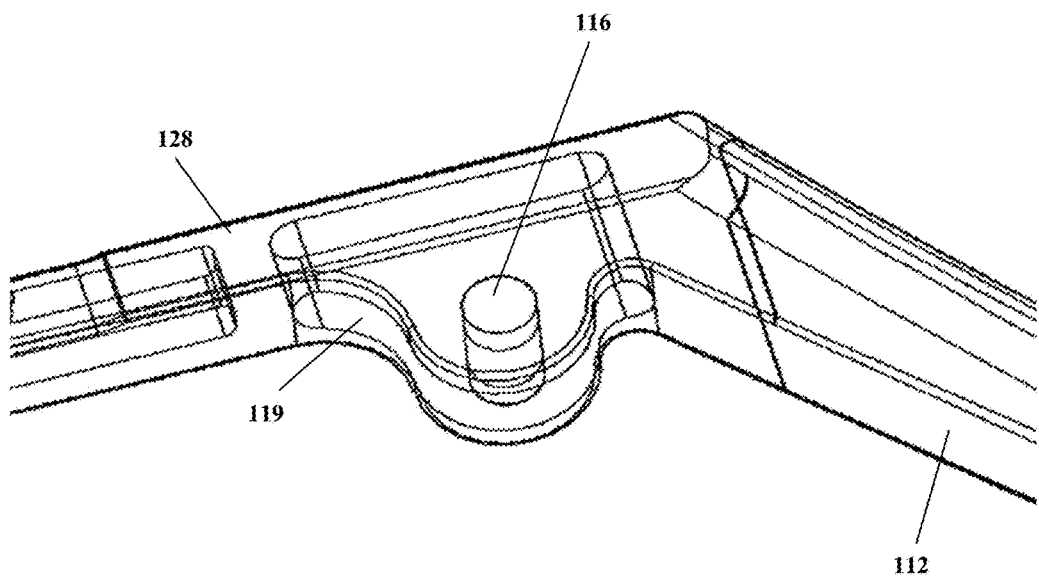
FIG. 6B is a perspective bottom view of the first handle coupled with the bottom rail portion.

As shown in FIG. 6B, the first handle 112 connects with the bottom rail portion 128 to form a slotted region 119 at the distal portion of the first handle 112 and the proximal end of the bottom rail portion 128. In one embodiment, the first handle 112 and the bottom rail portion 128 may be integral pieces. The slotted region 119 includes a width as to receive the distal end of the second handle 114 and an aperture to receive pin 116, such that the second handle 114 is able to rotate about pin 116 and within the slotted region 119.

Figure 7A:
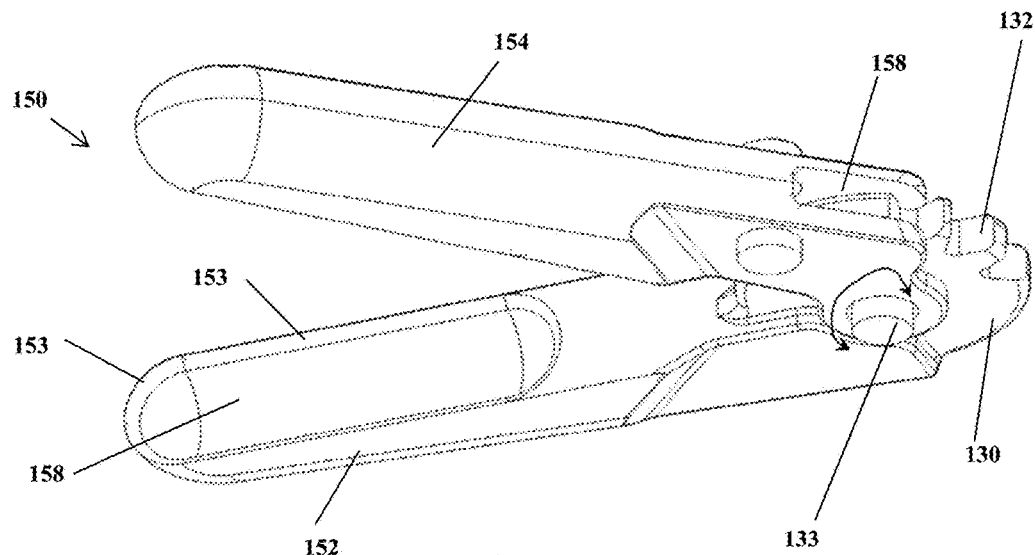
FIG. 7A is a perspective top view of the jaw portion in the open position.

The jaw portion 150 is shown in FIG. 7A, whereby the first jaw 152 and the second jaw 152 may include a grooved portion 156 by which to remove tissue. The second jaw 154 may include a slotted portion 158 on the proximal end, such as to couple to the ratchet 130 and allow the second jaw 154 to rotate to the open position relative to the first jaw 152. In one embodiment, the first jaw 152 and the second jaw 154 include sharpened edges 153 surrounding the grooved portion 156. The sharpened edges 153 serve to gouge or cut tissue or bone. Alternatively, the grooved portion 156 may be surrounded by teeth or other sharpened features to assist in the removal of bone or tissue.

Figure 7B:
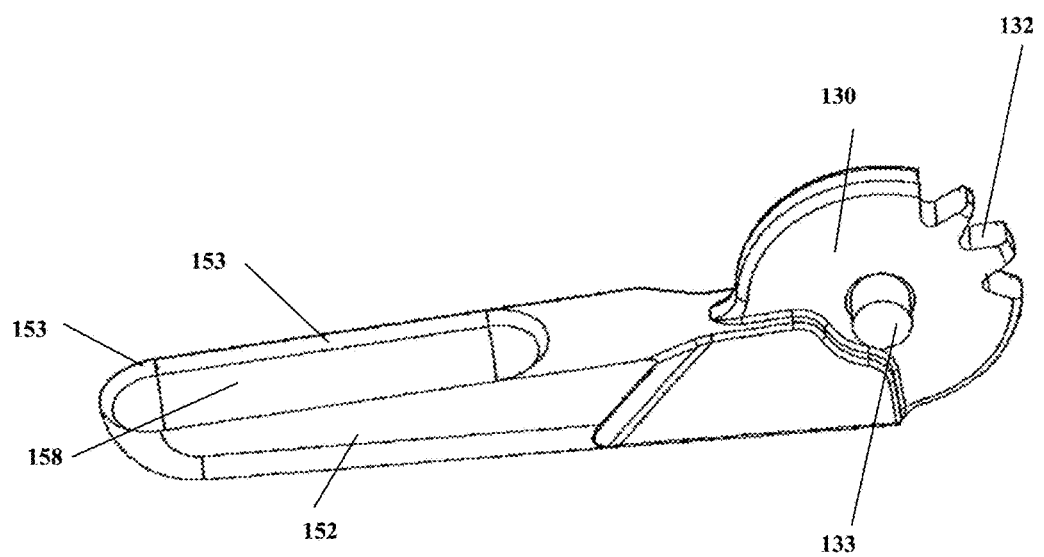
FIG. 7B is a perspective top view of the first jaw and the ratchet.

As shown in FIG. 7B, the first jaw 152 is fixedly coupled with the ratchet 130. In one embodiment, the ratchet 130 is integrally formed with the proximal end of the first jaw 152, alternatively, the ratchet 130 may be separate piece and fused or sealed to the proximal end of the first jaw 152. The ratchet 130 may include any number of detents 132 along the circumference of the ratchet 130. The detents 132 may be located and positioned along the circumference of the ratchet 130 to provide the specific angled position of the jaw position from −100 degrees to +100 degrees relative to the longitudinal axis of the Variable Angle Surgical Instrument.

Figure 8A:
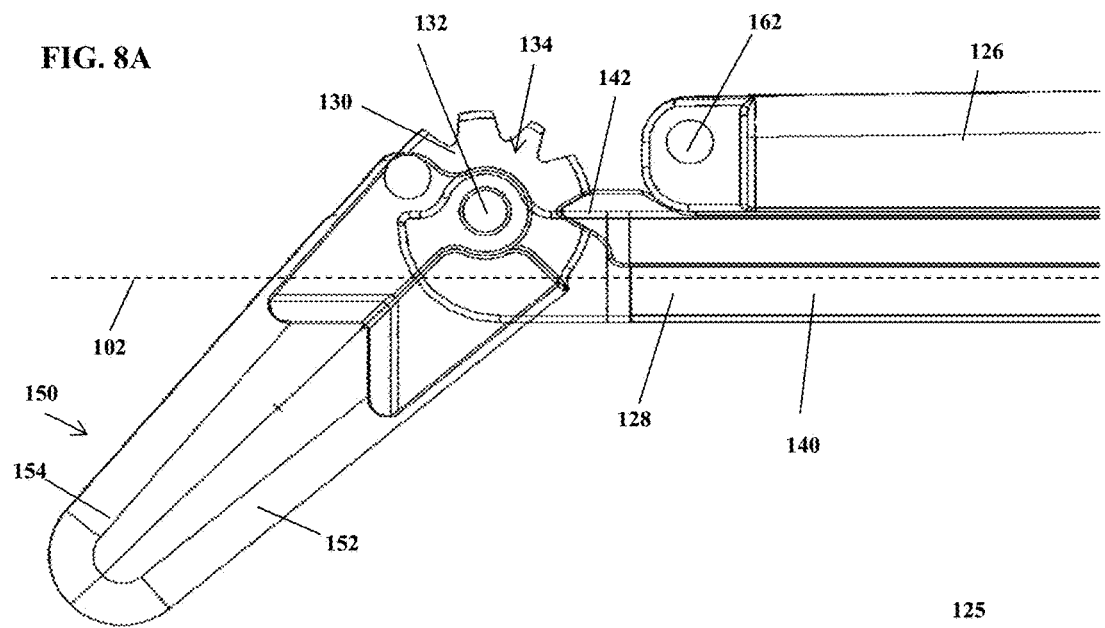
FIG. 8A is a side view of the jaw portion rotated to the −45 degree angle position whereby the link arm is removed.
Figure 8B:
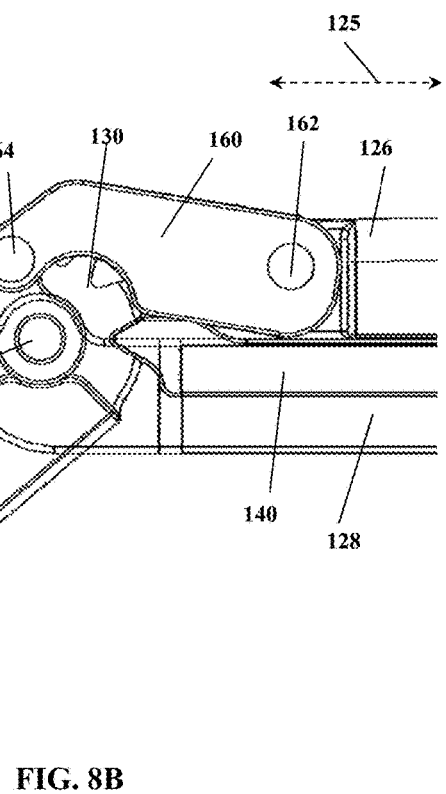
FIG. 8B is a side view of the jaw portion rotated to the −45 degree angle position with respect to the longitudinal axis, whereby the jaw portion is in the open position.

As shown in FIG. 8A, the jaw portion 150 is able to rotate in the negative degree with respect the longitudinal axis 102 of the Variable Angle Surgical Instrument. The jaw portion 150 rotates about pin 132 that is operably coupled with the bottom rail portion 128 and when the adjustment rod 140 is translated proximally towards the handle and the lip portion 142 of the adjustment rod 140 disengages from the detent 134 as to allow the ratchet 130 and the jaw portion 150 to rotate counterclockwise. In this embodiment, the jaw portion 150 is rotated to a −45 degree angle with respect to the longitudinal axis 102 and the lip portion 142 engages a detent 134 as to lock the jaw portion 150 into a −45 degree angle. Then the user operates the second handle 114, as shown previously, to longitudinally translate the top rail portion 126 towards the proximal end of the Variable Angle Surgical Instrument 100, as shown by arrow 125 in FIG. 8B. The top rail portion 126 serves to open the jaw portion 150 by rotating the second jaw 154 about pin 132 as generally shown by arrow 155. Link arm 160 is operably coupled to the top rail portion 126 by way of pin 162 disposed on the distal end of the top rail portion 126 and pin 164 disposed on the proximal end of the second jaw 154. The top rail portion 126 may be translated distally by operation of the second handle as to close the jaw portion 150 and the second jaw once tissue or desirable material is located between the first jaw 152 and second jaw 154.

Figure 9A:
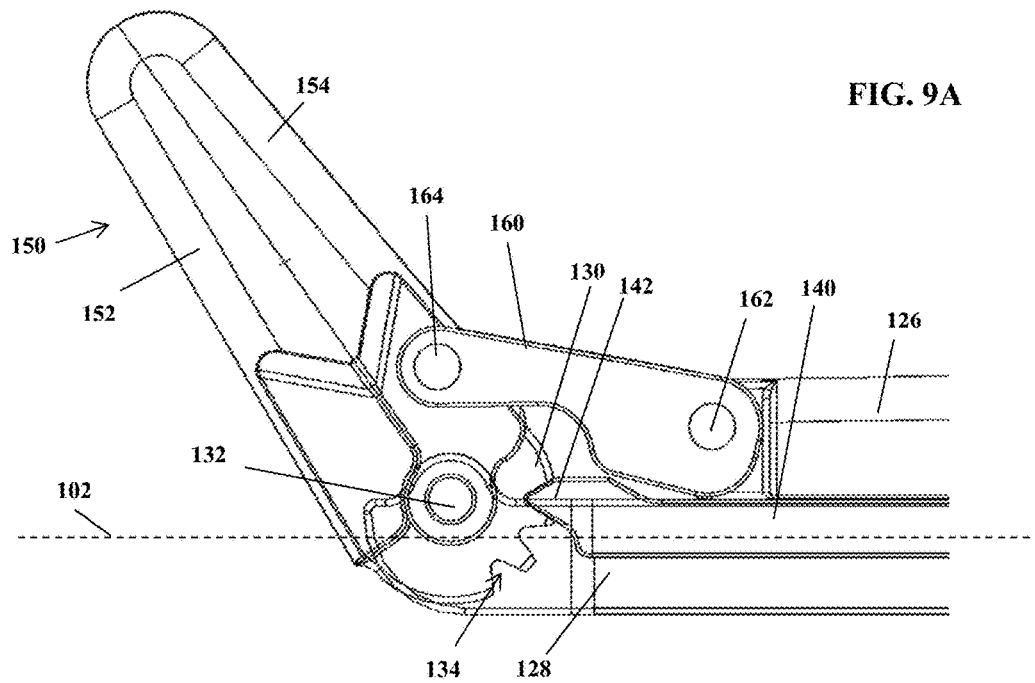
FIG. 9A is a side view of the jaw portion rotated to the 55 degree angle position with respect to the longitudinal axis, whereby the jaw portion is in the closed position.

As shown in FIG. 9A, the jaw portion 150 is able to rotate in the towards a 55 degree position with respect to the longitudinal axis 102 of the Variable Angle Surgical Instrument.

Figure 9B:
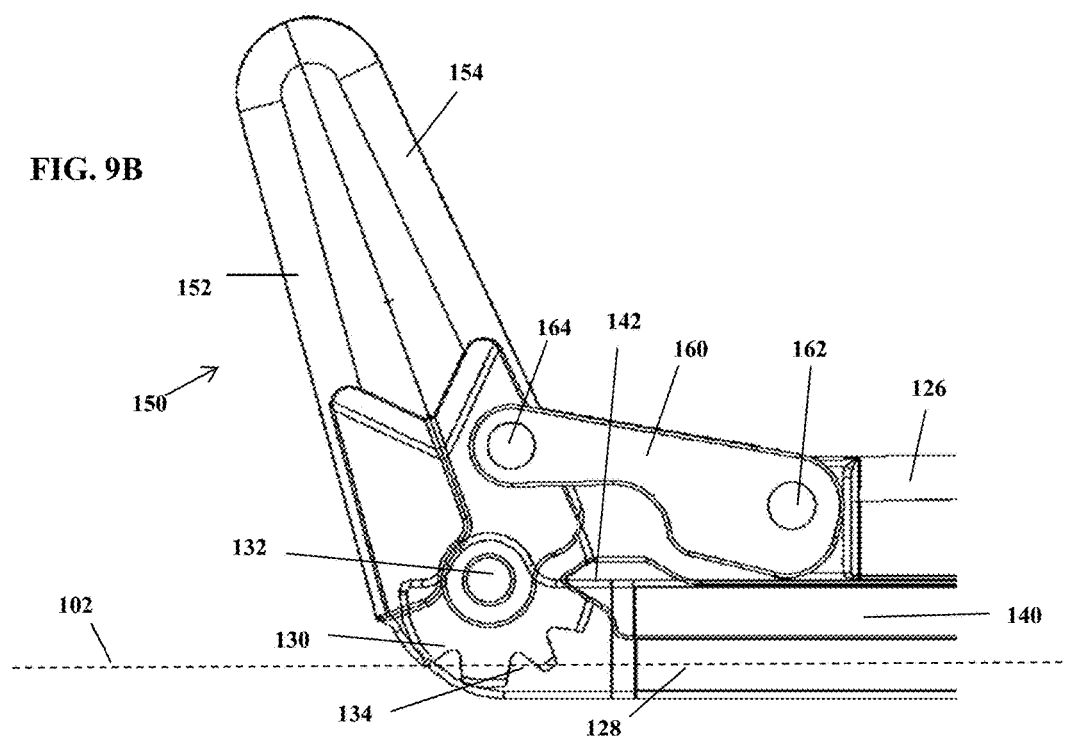
FIG. 9B is a side view of the jaw portion rotated to the 70 degree angle position with respect to the longitudinal axis, whereby the jaw portion is in the closed position.

The jaw portion 150 rotates about pin 132 that is operably coupled with the bottom rail portion 128 and when the adjustment rod 140 is translated proximally towards the handle and the lip portion 142 of the adjustment rod 140 disengages from the detent 134 as to allow the ratchet 130 and the jaw portion 150 to rotate counterclockwise. In this embodiment, the jaw portion 150 is rotated to a +55 degree angle with respect to the longitudinal axis 102 and the lip portion 142 engages a detent 134 as to lock the jaw portion 150 into a +55 degree angle. In another embodiment, the jaw portion 150 is rotated to a +70 degree angle position with respect to the longitudinal axis 102 of the Variable Angle Surgical Instrument, as shown in FIG. 9B.

Figure 10:
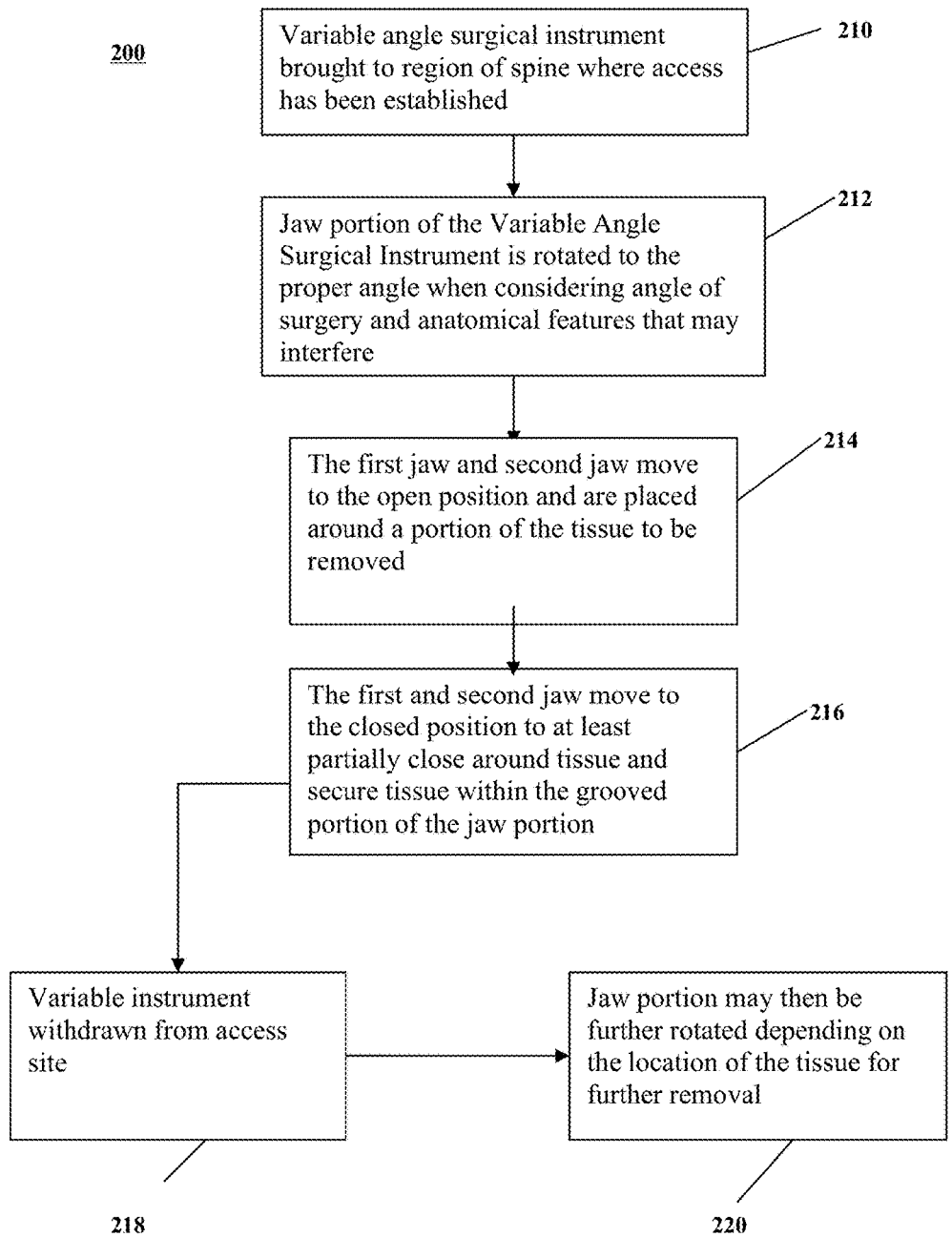
FIG. 10 is a flow chart for the method of using the variable angle surgical instrument.

FIG. 10 generally shows the method of removing tissue or bone by the Variable Angle Surgical Instrument 200. The Variable Angle Surgical Instrument is brought to a region of spine that requires tissue to be removed in step 210. The jaw portion of the Variable Angle Surgical Instrument is rotated to the proper angle when considering angle of surgery and anatomical features that may interfere in step 212. Then the first jaw and second jaw move to the open position and are placed around a portion of the tissue to be removed in step 214. Then the first and second jaw move to the closed position to at least partially close around tissue and secure tissue within the grooved portion of the jaw portion in step 216. The Variable Angle Surgical Instrument may then be removed from the surgical access site in step 218. Then depending on how much tissue that still requires removal, the jaw portion may then be further rotated depending on the location of the tissue for further removal in step 220.

As can be understood by one skilled in the art, the Variable Angle Surgical Instrument 100 and/or any of its components may have any size, shape, length, thickness, height, weight, or any other parameters. Such parameters may be selected by the surgeon (or other qualified professional) for performance of specific procedures. Further, the Variable Angle Surgical Instrument and/or any of its components may be manufactured from metal, plastic, synthetic material, or other suitable materials, or any combination thereof. In one embodiment, the Variable Angle Surgical Instrument 100 is composed of a metal alloy, titanium, nitinol, or stainless steel, or alternatively, any medical grade composite or ceramic.

In some embodiments, various lengths and configurations may also include various features to accommodate different applications for the Variable Angle Surgical Instrument. The Variable Angle Surgical Instrument can be constructed of various materials to aid in radio translucency, strength, flexibility, and integration with anatomy, etc.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A Variable Angle Surgical Instrument comprises: a rail portion including a proximal end, a distal end, and a longitudinal axis extending therebetween; a jaw portion coupled to the distal end of the rail portion; wherein the jaw portion rotates to variable angles relative to the longitudinal axis, and the jaw portion operates between a closed position and an open position to clamp down and remove tissue; a locking mechanism coupled to the rail portion to lock the jaw portion to an angled position;

a handle coupled with the proximal end of the rail portion, whereby the handle operates to move the jaw portion from the closed position to the open position;

wherein the rail portion includes top rail portion coupled with a bottom rail portion; the handle includes a first handle rotatably coupled with a second handle; the first handle coupled with the bottom rail portion and the second handle is coupled with the top rail portion; wherein the second handle rotates about the first handle as to longitudinally translate the top rail portion along the longitudinal axis as to open the jaw portion;

wherein the jaw portion comprises a first jaw rotatably coupled with a second jaw; wherein the first jaw is rotatably coupled with the bottom rail portion; the first jaw and the second jaw rotate together by way of a ratchet fixedly coupled with the first jaw;

an adjustment rod coupled within the bottom rail portion; the adjustment rod coupled with the ratchet and the adjustment rod translates longitudinally or along the longitudinal axis as to engage a first detent disposed along a circumference of the ratchet and locks a rotational position of the ratchet; wherein the ratchet is rotatably coupled with a pin connected to the bottom rail portion;

wherein the second jaw is rotatably coupled with a link arm; the link arm coupled with a distal end of the top rail portion as to open and rotate the second jaw with respect to the first jaw when the top rail portion translates longitudinally by rotation of the second handle;

wherein jaw portion rotates above the longitudinal axis to about 100 degrees and the jaw portion rotates below the longitudinal axis to about 100 degrees;

wherein the bottom rail portion includes a longitudinal cavity extending from the proximal end to the distal end of the bottom rail portion, whereby the adjustment rod is disposed within the longitudinal cavity and able to longitudinally translate towards the proximal end and the distal end of the bottom rail portion wherein the adjustment rod includes a proximal portion coupled with the locking mechanism and the bottom rail portion; the proximal portion of the adjustment rod includes a second detent and a button; the button protrudes from a grooved region disposed through a surface of the bottom rail portion, such that the button is able to longitudinally slide towards the proximal end of the bottom rail portion; the second detent locks into a hole disposed on an inner surface of the bottom rail portion, such that the second detent and hole serve to lock the adjustment rod from longitudinally moving; and the second detent and button are both disposed on top of a spring tab, which serves to bias the second detent towards the hole and the button towards an exterior surface of the bottom rail portion; and a spring coupled with the proximal end of the adjustment rod and the proximal end of the bottom rail portion, wherein the spring serves to bias the adjustment rod towards the distal end of the bottom rail portion.

2. The Variable Angle Surgical Instrument of claim 1, wherein displacement of the button towards an interior of the adjustment rod displaces the second detent from the hole to permit translation of the adjustment rod towards the proximal end of the Variable Angle Surgical Instrument and allows the jaw portion to rotate to its desired angle position by disengaging a lip portion of the adjustment rod from the first detent of the ratchet.

3. The Variable Angle Surgical Instrument of claim 2, wherein the second handle include a top slotted portion coupled with the proximal end of the top rail portion; the proximal end of the top rail portion includes a slotted portion and a pinned portion, by which the second handle longitudinally translates the top rail portion by rotation of the second handle about the first handle and the distal end of the second handle translates the top rail portion.

4. The Variable Angle Surgical Instrument of claim 3, wherein the first handle connects with the bottom rail portion to form a second slotted region at the distal portion of the first handle and the proximal end of the bottom rail portion; wherein the second slotted region of first handle includes an aperture to receive a second pin, such that the second handle is able to rotate about the second pin and within the second slotted region.

5. The Variable Angle Surgical Instrument of claim 4, whereby the first jaw and the second jaw include a plurality of grooved portions by which to remove tissue.

6. The Variable Angle Surgical Instrument of claim 5, wherein the second jaw includes a slotted portion on the proximal end as to receive the ratchet and to allow the second jaw to rotate to the open position relative to the first jaw.

7. The Variable Angle Surgical Instrument of claim 6, wherein the first detent is located and positioned along the circumference of the ratchet to provide a specific angled position of the jaw portion from about −100 degrees to +100 degrees relative to the longitudinal axis of the Variable Angle Surgical Instrument.

8. A method of using a Variable Angle Surgical Instrument of claim 1, comprising: disengaging an adjustment rod coupled with a ratchet and a jaw portion and rotating the jaw portion of the Variable Angle Surgical Instrument to a proper angle relative to the longitudinal axis of the Variable Angle Surgical Instrument; opening the jaw portion by longitudinally translating a top rail portion towards the proximal end of the Variable Angle Surgical Instrument by rotation of a handle; placing the opened jaw portion around a portion of the tissue to be removed; moving the jaw portion to a closed position to at least partially close around tissue and secure tissue within a grooved portion of the jaw portion.

9. A Variable Angle Surgical Instrument comprises: a rail portion including a proximal end, a distal end, and a longitudinal axis extending therebetween; a jaw portion coupled to the distal end of the rail portion; wherein the jaw portion rotates to variable angles relative to the longitudinal axis, and the jaw portion operates between a closed position and an open position to clamp down and remove tissue; a locking mechanism coupled to the rail portion to lock the jaw portion to an angled position; wherein the rail portion includes top rail portion coupled with a bottom rail portion;

wherein the jaw portion comprises a first jaw rotatably coupled with a second jaw; wherein the first jaw is rotatably coupled with the bottom rail portion; the first jaw and the second jaw rotate together by way of a ratchet fixedly coupled with the first jaw;

an adjustment rod coupled within the bottom rail portion; the adjustment rod coupled with the ratchet and the adjustment rod translates longitudinally or along the longitudinal axis as to engage a first detent disposed along a circumference of the ratchet and locks a rotational position of the ratchet; wherein the ratchet is rotatably coupled with a pin connected to the bottom rail portion;

wherein the adjustment rod includes a proximal portion coupled with the locking mechanism and the bottom rail portion; the proximal portion of the adjustment rod includes a second detent and a button; the button protrudes from a grooved region disposed through a surface of the bottom rail portion, such that the button is able to longitudinally slide towards proximal end of the bottom rail portion; the second detent locks into a hole disposed on an inner surface of the bottom rail portion, such that the second detent and hole serve to lock the adjustment rod from longitudinally moving; and the detent and button are both disposed on top of a spring tab, which serves to bias the second detent towards the hole and the button towards an exterior surface of the bottom rail portion; and a spring coupled with the proximal end of the adjustment rod and the proximal end of the bottom rail portion, wherein the spring serves to bias the adjustment rod towards the distal end of the bottom rail portion.

10. The Variable Angle Surgical Instrument of claim 9, further comprising a handle coupled with the proximal end of the rail portion, whereby the handle operates to move the jaw portion from the closed position to the open position; the handle includes a first handle rotatably coupled with a second handle; the first handle coupled with the bottom rail portion and the second handle is coupled with the top rail portion; wherein the second handle rotates about the first handle as to longitudinally translate the top rail portion along the longitudinal axis as to open the jaw portion.

11. The Variable Angle Surgical Instrument of claim 10, the second jaw is rotatably coupled with a link arm; the link arm coupled with a distal end of the top rail portion as to open and rotate the second jaw with respect to the first jaw when the top rail portion translates longitudinally by rotation of the second handle; wherein jaw portion rotates above the longitudinal axis to at about 100 degrees and rotates below the longitudinal axis to about 100 degrees.

12. The Variable Angle Surgical Instrument of claim 11, the bottom rail portion includes a longitudinal cavity extending from the proximal end to the distal end of the bottom rail portion, whereby the adjustment rod is disposed within the longitudinal cavity and is able to longitudinally translate towards the proximal end and distal end of the bottom rail portion.

* * * * *